(12) United States Patent
Modi (10) Patent No.: US 8,597,257 B2
(45) Date of Patent: Dec. 3, 2013

(54) DRUG DELIVERY DEVICE

(75) Inventor: Pankaj Modi, Ancaster, CA (US)

(73) Assignee: PKA Softtouch Corp., Lakefield, Ontario (CA)

( * ) Notice: Subject to any disclaimer, the term of this patent is extended or adjusted under 35 U.S.C. 154(b) by 64 days.

(21) Appl. No.: 13/229,538

(22) Filed: Sep. 9, 2011

(65) Prior Publication Data

US 2011/0319834 A1 Dec. 29, 2011

Related U.S. Application Data

(63) Continuation of application No. 11/355,000, filed on Feb. 16, 2006, now abandoned.

(51) Int. Cl.
| *A61M 5/178* | (2006.01) |
| *A61M 5/00* | (2006.01) |
| *A61M 5/20* | (2006.01) |
| *A61M 5/32* | (2006.01) |
| *A61M 5/315* | (2006.01) |

(52) U.S. Cl.
USPC .......... 604/214; 604/117; 604/139; 604/192; 604/110; 604/228

(58) Field of Classification Search
USPC .......... 604/19, 48, 93.01, 110, 131, 132, 139, 604/141–146, 156–157, 167.01, 167.02, 604/181, 185–189, 197, 201, 232, 246–249
See application file for complete search history.

(56) References Cited

U.S. PATENT DOCUMENTS

| 2,371,086 | A | | 3/1945 | Edward et al. |
| 2,667,872 | A | * | 2/1954 | Smith ........................... 604/192 |
| 3,527,215 | A | * | 9/1970 | De Witt ......................... 604/214 |
| 4,883,473 | A | | 11/1989 | Thomas |
| 4,886,499 | A | | 12/1989 | Cirelli et al. |
| 4,955,871 | A | * | 9/1990 | Thomas ......................... 604/217 |
| 5,527,288 | A | | 6/1996 | Gross et al. |
| 5,658,259 | A | * | 8/1997 | Pearson et al. ................ 604/232 |
| 5,931,814 | A | * | 8/1999 | Alex et al. ..................... 604/131 |
| 5,964,736 | A | | 10/1999 | Lane |
| 5,997,501 | A | | 12/1999 | Gross et al. |
| 6,102,896 | A | * | 8/2000 | Roser ............................ 604/218 |
| 6,387,078 | B1 | * | 5/2002 | Gillespie, III ................. 604/181 |
| 6,494,865 | B1 | * | 12/2002 | Alchas ........................... 604/192 |
| 6,569,143 | B2 | | 5/2003 | Alchas et al. |
| 6,607,509 | B2 | * | 8/2003 | Bobroff et al. ................ 604/136 |
| 6,620,134 | B1 | | 9/2003 | Trombley et al. |
| 6,689,118 | B2 | | 2/2004 | Alchas et al. |
| 6,808,507 | B2 | | 10/2004 | Roser |
| 6,896,666 | B2 | * | 5/2005 | Kochamba .................... 604/141 |
| 6,979,316 | B1 | * | 12/2005 | Rubin et al. ................... 604/156 |
| 2005/0124967 | A1 | | 6/2005 | Kaestner et al. |
| 2006/0229562 | A1 | * | 10/2006 | Marsh et al. ............. 604/164.01 |

FOREIGN PATENT DOCUMENTS

| CA | 2126320 | 1/1993 |
| CA | 2328158 | 10/1999 |
| CA | 2376147 | 1/2001 |

(Continued)

*Primary Examiner* — Kevin C Sirmons
*Assistant Examiner* — William Carpenter (57) ABSTRACT

A novel device and method for intradermal delivery of an active agent is provided. The device comprises a housing which contains a reservoir chamber. A flexible reservoir containing the active agent is placed in the chamber. Upon pressure on an actuator the active agents is delivered via a hollow needle to the skin.

13 Claims, 12 Drawing Sheets

(56) References Cited

FOREIGN PATENT DOCUMENTS

| CA | 2536854 | 2/2006 |
| CA | PCT/CA2007/000225 | 5/2007 |
| CA | PCT/CA2007/00225 | 8/2009 |
| EP | 0330785 | 9/1989 |
| EP | 0652027 A1 | 5/1995 |
| EP | 1452196 | 9/2004 |
| EP | 1 983 964 | 4/2009 |
| WO | WO 03/037410 A1 | 5/2003 |
| WO | WO 2006129196 A1 * | 12/2006 |

* cited by examiner

DRUG DELIVERY DEVICE

REFERENCE TO RELATED APPLICATION

The present application is a Continuation of U.S. patent application Ser. No. 11/355,000, filed Feb. 16, 2006, entitled "DRUG DELIVERY DEVICE" and assigned U.S. Patent Application Number US-2007/0191780-A1, the entire contents of which is incorporated herein by reference.

FIELD OF INVENTION

The present invention relates to drug delivery devices and methods of delivering a drug intradermally. In particular, the present invention relates to intradermal delivery of a liquid drug.

BACKGROUND OF THE INVENTION

There has long been a desire to deliver drugs intradermally. The skin comprises two layers, the outer or upper surface called the epidermis, and the internal surface referred to as the dermis. The epidermis does not contain any blood vessels and it is dependent on the underlying dermis for nutrient delivery and waste disposal via diffusion. The inner layer, the dermis, is composed of two layers, the more superficial papillary dermis and the deeper reticular dermis. The papillary dermis is thinner and consists primarily of loose connective tissue containing small capillaries, elastic fibers, reticular fibers and some collagen. The deeper reticular dermis consists of a thicker connective tissue containing larger blood vessels, interlaced elastic fibers and core spindles of collagen fibers arranged in layers parallel to the surface. The reticular layer also contains many antigen-presenting cells, fibroblasts, mast cells, nerve endings, and lymphatics. Because of the high amount of blood vessels, lymphatics and antigen presenting cells in the dermis, this is an ideal site for delivery of drugs and/or antigens.

A major problem, however, with intradermal delivery is the difficulty in precisely delivering the drug into the dermal layer. Generally, the outer layer, the epidermis, has a thickness of about 0.05 to 2 mm and the dermis has a thickness between about 1.5 and 4 mm. Thus, to deliver an agent to the dermis, the needle must penetrate the skin to a depth of no more than 5 mm, preferably between about 2 and 4 mm. It is very difficult to control an injection to this shallow depth. For certain types of injection, such as the Mantoux test for tuberculosis, a fine gauge needle is inserted at a 45° angle to try and get the agent into the dermis.

Several efforts have been made to try and find reliable ways of delivering agents to the dermis. For example, United States Patent Application No. 2005/0124967 is directed to a method for directly delivering a high molecular weight substance into an intradermal space within mammalian skin comprising administering the substance through at least one hollow needle having an outlet with an exposed height between 0 and 1 mm, said outlet being inserted into the skin to a depth of between 0.3 mm and 2 mm, such that delivery of the substance occurs at a depth between 0.3 mm and 2 mm and a microneedle for intradermal injection of a high molecular weight pharmaceutical substance, wherein the microneedle has a length and outlet selected for its suitability for specifically delivering the substance into the dermis.

U.S. Pat. No. 5,527,288 discloses an intradermal drug delivery device for delivering a liquid drug to a subject via the subject's skin, comprising a housing having a lower surface for application to the skin of the subject; means for affixing the housing in position with the lower surface in contact with the subject's skin; and a drug reservoir within the housing. The reservoir is in the form of an expansible-contractible chamber which is expanded when filled with the drug and which can be contracted to dispense the drug therefrom. A single hollow needle is associated with the drug reservoir and extends through the lower surface, having an inner end communicating with the drug reservoir and an outer end projecting outwards a sufficient distance so as to penetrate through the epidermis and into the dermis when the housing is pressed against the skin. The device also includes means for actively discharging the drug from the reservoir to the subject's skin via the needle.

U.S. Pat. No. 6,689,118 is directed to a method of making an intradermal injection into the skin of an animal to obtain systemic delivery or to induce an immune response. The method comprises providing a drug delivery device including a needle cannula having a forward needle tip and a needle cannula being in fluid communication with a substance contained in said drug delivery device; inserting the needle tip into the skin of an animal and engaging the surface of the skin with a skin engaging surface of a limiter portion such that the skin engaging surface of the limiter portion limits penetration of the needle tip into the dermis layer of the skin of the animal; and expelling the substance from the drug deliver device through the needle tip into the skin of the animal to expose the injected substance to the microcirculatory blood vasculature and the lymphatic plexuses.

U.S. Pat. No. 6,569,143 is directed to another related method of making an intradermal injection comprising providing a drug delivery device; inserting a needle tip into the skin of an animal whereby penetration of the needle tip is limited to the dermis layer of the skin of the animal; and expelling the substance from said drug delivery device through the needle tip into the skin of the animal.

U.S. Pat. No. 5,997,501 describes an intradermal drug delivery device for the delivery of at least one drug to a subject via the subject's skin. The device comprises a housing having a lower surface; a drug reservoir located with the housing; a cover that is adjustable engaged with the housing from a first extended position to a second retracted position such that the cover is proximal to the lower surface of the housing when the cover is retracted and the cover is distal to the lower surface of the housing when the cover is extended; means for affixing the cover in position with the lower surface of the housing in contact with the subject's skin; a single hollow needle fixed to the cover and having a first end in communication with the drug reservoir and a second end projecting outwards no further than the lower surface of the housing when the cover is extended, and to penetrate through the epidermis and into the dermis when the cover is retracted; and means for actively discharging the drug from the reservoir to the subject's skin via the needle.

Although multiple efforts have been made to try and provide a device for intradermal delivery, many of the prior art devices are expensive to manufacture or can only be used for one drug. In spite of all the efforts made to provide a method and/or device for intradermal delivery, there remained a need for a reliable, single-use, disposable device for intradermal delivery.

SUMMARY OF THE INVENTION

Many people consider an injection (at best) unpleasant and (at worst) a painful encounter, no matter how well the nurse or doctor administers the shot. This is because most shots are given subcutaneously or intramuscularly, reaching deep enough into the skin to hit nerves. Part of the skin's job is to sense danger in the environment through nerve cells, and it is richly endowed with these cells—a single square inch of skin contains approximately 1,300 nerve endings. Since most injections are given subcutaneously or intramuscularly, thereby delivering drugs to be absorbed into the blood vessels, the needle generally strikes nerves and causes pain along the way. The device of the present invention is based on a unique technology that allows a liquid pharmaceutical formulation to be delivered into the skin of the patients through a fine needle without the significant pain experienced by regular injection needles. The drug is injected into the layers of the skin, avoiding the pinching of the nerves. This reduces pain significantly or eliminates it totally in many cases thus improving the acceptance and compliance to treat many diseases like diabetes.

The present invention addresses the problems of the prior art by providing a novel type of reservoir for a drug and a delivery device for delivering the drug from the reservoir to a specific depth of skin. A method of preparing the drug reservoir and a method of delivering a fluid drug are also provided.

In one aspect of the invention a reservoir for carrying an active agent is provided. The reservoir comprises a fillable bladder having flexible walls that can be sealed.

A method of manufacturing such a reservoir is also provided. In one embodiment, the method comprises the steps of: opposing two layers of thermoplastic film; heating the film; applying a vacuum mold to the outer surface of each layer of film to form a bubble; and allowing the film to cool.

In another embodiment, the method comprises preparing a sheet of thermoplastic material having a series of wells or depressions as fillable reservoirs. A top sheet is then applied to seal the reservoirs.

A method of filling the reservoir is also provided and comprises filling the bladder with a fluid drug; and sealing the reservoir.

In another aspect of the invention, a device for delivery of a fluid drug to an animal is provided. The term "animal" is used herein to include both human and non-human animals. The devices and methods of the invention are applicable for both human and veterinary use. The device comprises a housing having an upper end and a lower end, the lower end having an aperture therein and the upper end being adapted to receive a drive actuator. A reservoir chamber is disposed within the housing and operatively linked to the drive actuator. The reservoir chamber has a base and wall(s). The wall may be a continuous circular wall or a connected set of walls. Within the reservoir chamber, there is a flexible reservoir filled with the fluid drug. A microneedle is mounted on the base so as to transverse the base of the chamber such that the top of the needle is in communication with the chamber and the tip of the needle extends in the housing below the chamber.

In a preferred embodiment, the reservoir chamber is located at a predetermined distance from the lower end of the housing whereby abutment of the base of the chamber to the lower end of the housing acts as a stop to provide a predetermined length of travel of the needle through the aperture when the drive mechanism or actuator is activated. The length of travel is optimally set to deliver the drug intradermally. The device also preferably includes biasing means to maintain the reservoir chamber in the upper position within the housing, in the absence of pressure on the actuator thus retaining the needle tip inside the housing.

In another embodiment of the invention, the device includes a lower housing and an upper housing that fits over the lower housing. In this embodiment, the upper housing is continuous with the actuator that causes the reservoir to descend and contact the needle end.

In yet another aspect of the invention, a method of administering a fluid drug through the skin of an animal is provided. The method comprises providing a device as defined above; applying the lower surface of the device to the skin; exerting pressure on the drive mechanism thereby lowering the reservoir chamber and causing the needle tip to travel through the aperture and into the skin a predetermined distance; and applying continued pressure on the actuator to cause the upper end of the needle to pierce the reservoir and continuing to apply pressure so that all the contents of the reservoir flow through the needle into the skin.

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

The following description is of preferred embodiments.

In one aspect of the present invention a novel type of drug reservoir is provided. The drug reservoir comprises a fillable bladder. The reservoir is formed between two layers of plastic film. The two layers can be formed from two sheets or from one sheet folded in half. When two sheets are used, the sheets may comprise the same material, thickness, etc. or they may be two different types of sheets.

The present invention provides for a drug delivery device incorporating a disposable reservoir. The device may be provided as a single-use, disposable device or a multi-use device. The device comprises a housing that has an upper end and a lower end. As used herein, the term "upper" is used to refer to the surface furthest away from an individual skin and the term "lower" is used to refer to the part of the device that contacts a patient's skin. An actuator is mounted at the top of the housing. The actuator is used to activate a drive mechanism. One example of a drive mechanism is a plunger that travels up and down within the housing. A reservoir chamber is slideably mounted within the housing. The reservoir chamber holds a reservoir filled with a liquid. The reservoir chamber is operatively linked to the drive mechanism. The reservoir chamber has a micro needle mounted on the lower surface of the chamber. When the plunger is depressed, the reservoir housing travels downward within the housing until it stops when the bottom of the reservoir housing hits the bottom of the outer housing.

Figure 1A:
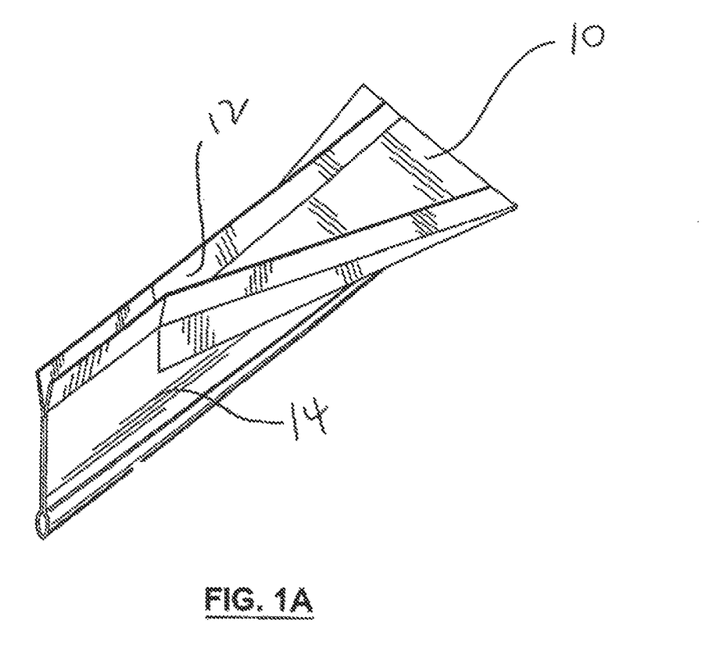
FIGS. 1A to 1G illustrate the steps in the manufacture of a drug reservoir according to the present invention.
Figure 1B:
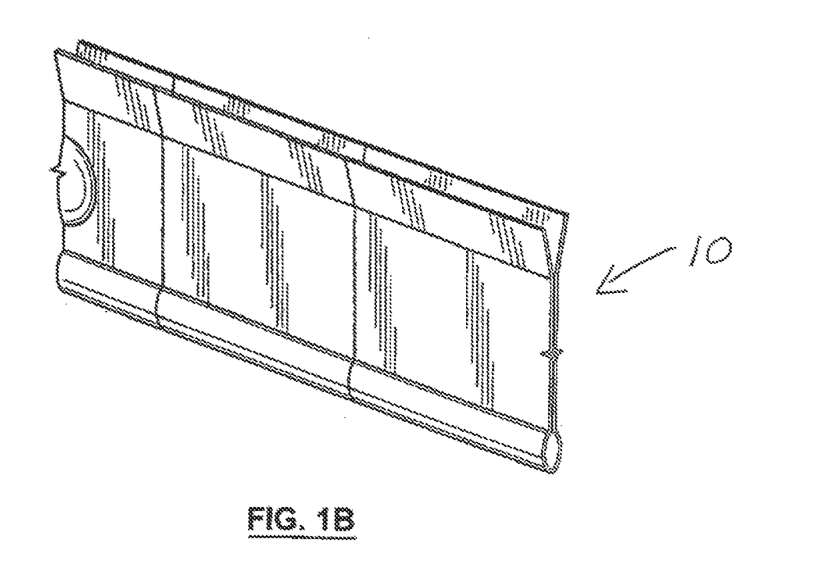
Figure 1C:
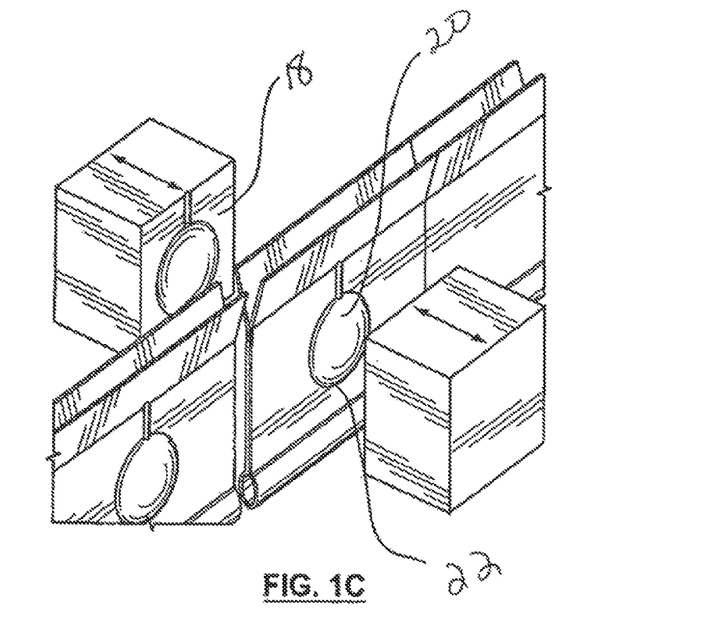
Figure 1D:
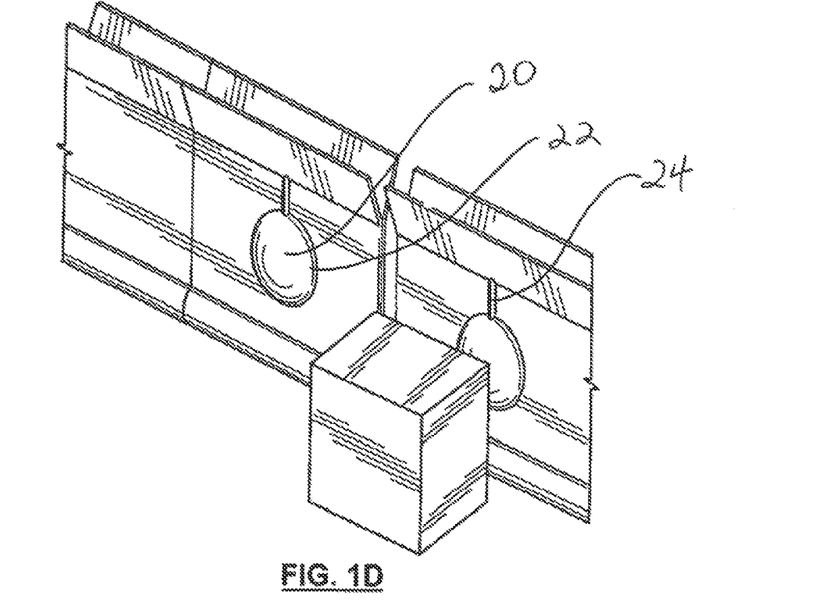
Figure 1E:
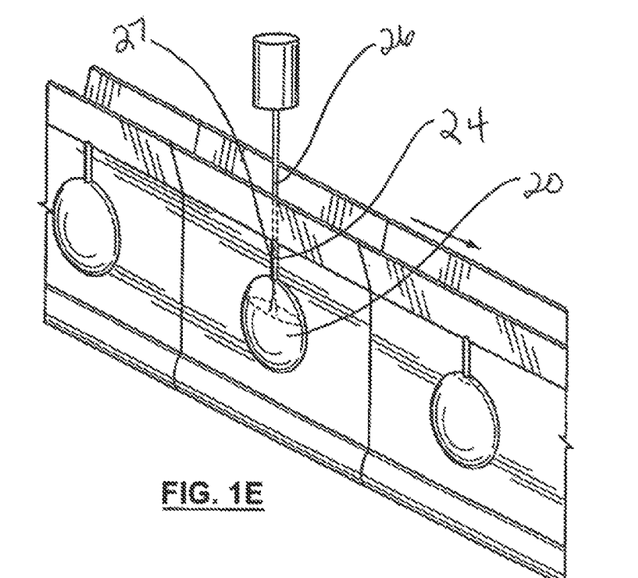
Figure 1F:
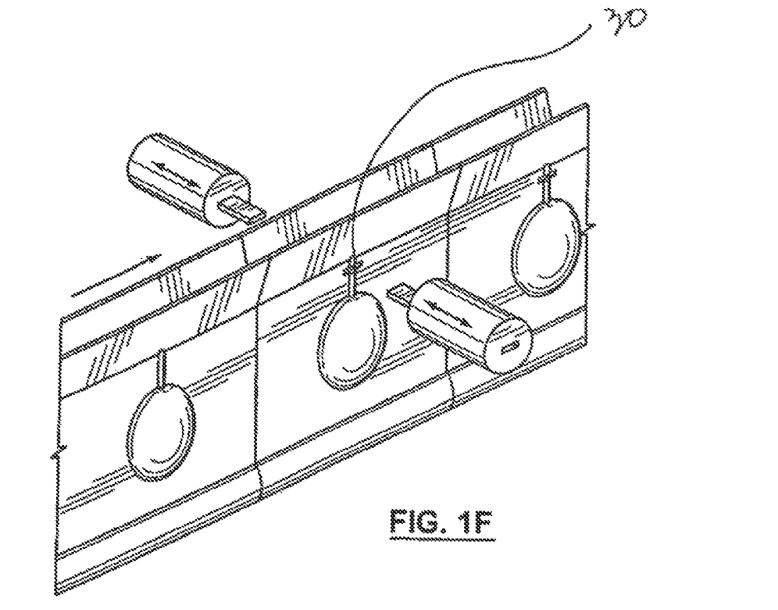
Figure 1G:
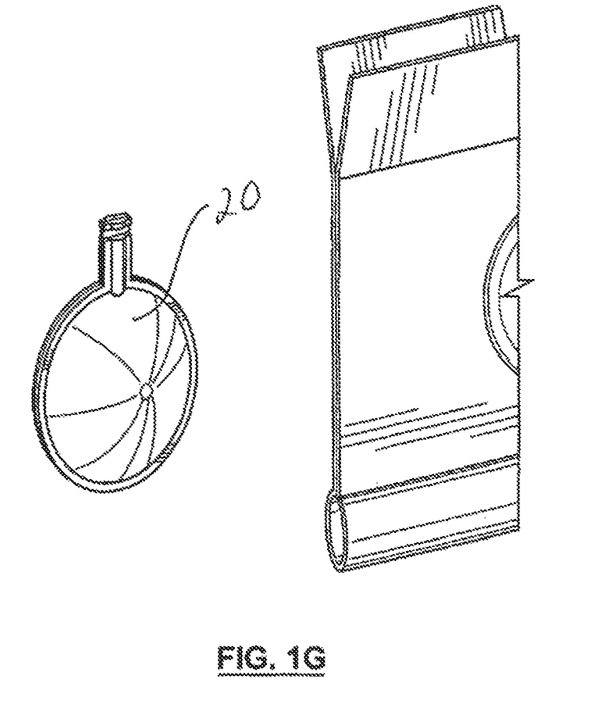

A process for the manufacture of one embodiment of the reservoir is shown in FIGS. 1A-G. In FIG. 1A, a sheet of thermoplastic material 10 is folded in half to provide a first surface 12 and a second surface 14. Referring to FIG. 1B, the sheet 10 is folded so that the first surface and the second surface overlap each other. Then the sheet is heated to soften the film. FIG. 1C illustrates a mold 18 applied to each of the surfaces 12, 14. The mold for each side may be of similar or different shapes. As a vacuum is applied to the mold halves, a bubble 20 is formed and at the same time the boundary 22 of the reservoir shape is sealed. A vertical path 24 is left open for filling of the reservoir. As shown in FIG. 1D, the mold halves 18 are removed and the sheet 10 including the bubbles 20 are cooled to room temperature. The filling process is demonstrated in FIG. 1E. The film is preferably oriented with the vertical path 24 open at the top for filling to avoid the formation of air pockets during the filling process. A fine dispensing nozzle 26 is inserted into the vertical path 24 and a controlled amount of drug 27 is inserted into the reservoir. The open end 30 of the vertical path 24 is then heat sealed as shown in FIG. 1F. The bubble shaped reservoir 20 can then be trimmed as shown in FIG. 1G from the remaining sheets of plastic film or the bubble shapes can be partially trimmed and the bubbles can be stored in a roll format.

In another embodiment, the reservoir is formed by preparing a sheet of material having a series of wells or depressions. The wells are filled with a drug and then an upper sheet is applied to cover and seal the open end of the wells. In both embodiments the reservoir comprises a fillable, sealable bladder of thermoplastic material.

Various colors and shapes of reservoirs can be used for different drugs. For example, a round, blue bubble may indicate that the reservoir contains insulin and a square pink bubble may indicate a DPT vaccine. The reservoir of the present invention can be used to store many different kinds of active agents. Color coding can be used to identify the agent and/or dose strength.

The present invention also provides a device and method for delivery of the drug stored in the reservoir to an animal, preferably a human. The device comprises an outer housing. The outer housing can be made of any durable material, preferably a hard plastic. The outer housing can take various shapes, e.g. it can be round, oval, hexagonal, square etc. The outer housing can incorporate various colours to identify the agent and/or dose strength. The outer housing defines an internal chamber that includes an open top at the upper end and a base having an aperture at the lower end. A reservoir chamber is fitted inside the housing. The reservoir chamber is adapted to receive a disposable reservoir such as that described above. A microneedle is mounted in the bottom platform of the reservoir chamber with its upper (non-skin contacting) end protruding upward and just below the reservoir and the skin-contacting tip extending beyond the bottom of the chamber. The reservoir chamber frictionally engages the internal wall(s) of the housing. A drug reservoir or bubble is contained within the reservoir chamber. A drive actuator is operatively linked to the reservoir chamber. The drive actuator may include a flexible dome or an upper casing. The reservoir chamber typically comprises an open upper end, an internal chamber to hold the reservoir and a base platform with the needle mounted so that it transects the base. A retraction mechanism such as a vacuum bulb or a spring is also optionally included.

In use, the delivery device is placed on the skin with the lower end of the housing touching the skin. The drive mechanism is then actuated to drive the reservoir chamber downwards until the base platform of the reservoir chamber hits the base of the housing. This causes the needle to exit through the aperture in the base of the housing a predetermined distance and enter into the skin to a predetermined depth. Further downward pressure on the plunger compresses the drug filled reservoir and causes it to be pierced by the upper end of the needle. This puts the cannula of the needle in fluid communication with the contents of the reservoir and as the downward pressure continues until the tip of the plunger bottoms on the base platform of the reservoir chamber, the contents of the reservoir are passed through the cannula of the needle to the skin of an animal or human subject. When the pressure on the drive mechanism is released, retraction means cause the needle to be retracted back into the housing for disposal.

One preferred embodiment of the device and its operation is shown in FIGS. 2A-J. The device 50 comprises housing 52. The housing has an open upper end 54 and a bottom base 56 defining an interior chamber 58 that optionally includes a spring. The bottom base comprises an aperture 60. The interior of the housing is adapted to receive a reservoir chamber 62 having a chamber ledge 62A circumferentially disposed around the interior of the upper end of the chamber 62. The reservoir chamber comprises a base 64 and a surrounding wall 66 extending upwards from the base defining a chamber 62 with an open top 68. A filled reservoir body 70 is located in the reservoir chamber.

Figure 2A:
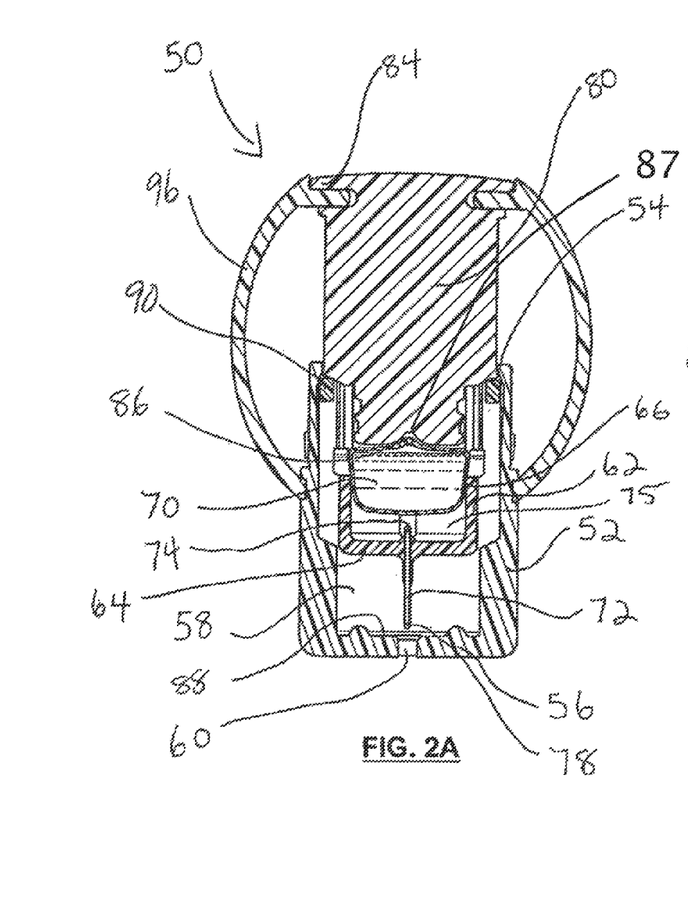
FIGS. 2A to 2J Illustrate the operation of one embodiment of a delivery device of the invention.
Figure 2B:
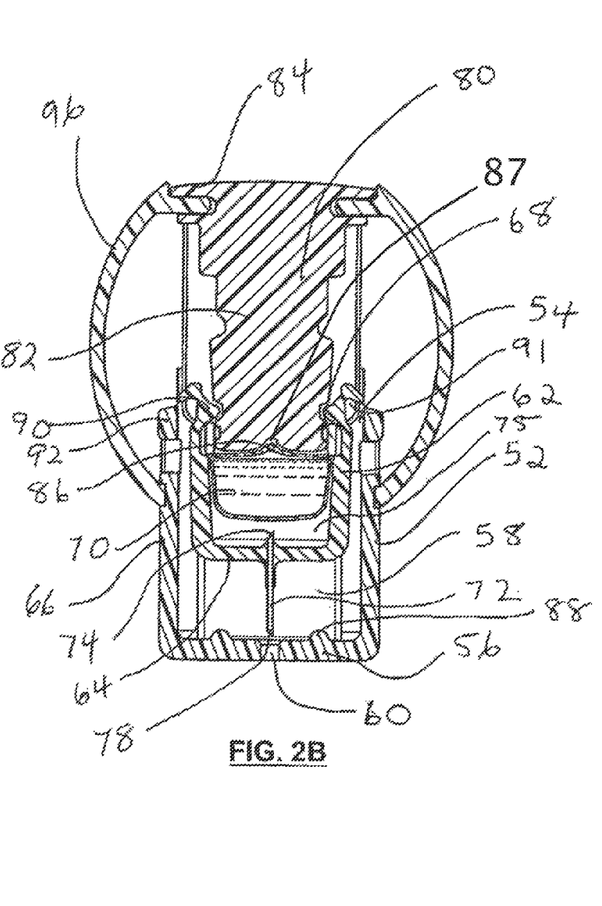

A single hollow needle 72 is associated with the reservoir chamber 62. The needle 72 extends through the base 64 of the chamber 62 and has a cannula with an upper end 74 communicating with the interior 75 of the reservoir chamber and a lower end 78 projecting out of the chamber and down a predetermined distance. The open top 68 of the reservoir chamber is adapted to receive an actuator 80. In the illustrated embodiment, the actuator comprises a plunger 82 having an activation flange 84 at one end and a stopper 86 at the other end. The stopper 86 includes a frustoconical depression formed therein, as depicted in FIGS. 2A-3B. In the initial position of the device as provided and as shown in FIGS. 2A and 2B, the base 64 of the reservoir chamber 62 is held at a predetermined distance from the interior surface 88 of the base 56 of the housing by at least one releasable latch 90 which retains the chamber in position by the interaction of the latch 90 with a latch retainer 92. The latch 90 includes a notch 91.

In one preferred embodiment an upper housing 96 encases the plunger 80.

It is clearly apparent that the distance the needle travels can be varied depending on the desired application and on the bubble position and the length of the needle. For example, the device can be adapted to have the needle travel a distance between about 0.5 mm to about 10 mm. Thus, the device of the invention can be adapted for intradermal, subcutaneous or intramuscular injections. The needle preferably travels from about 3 mm to 8 mm. The needle gauge is preferably 25 to 84 gauge although different gauge needles can be used.

Figure 2C:
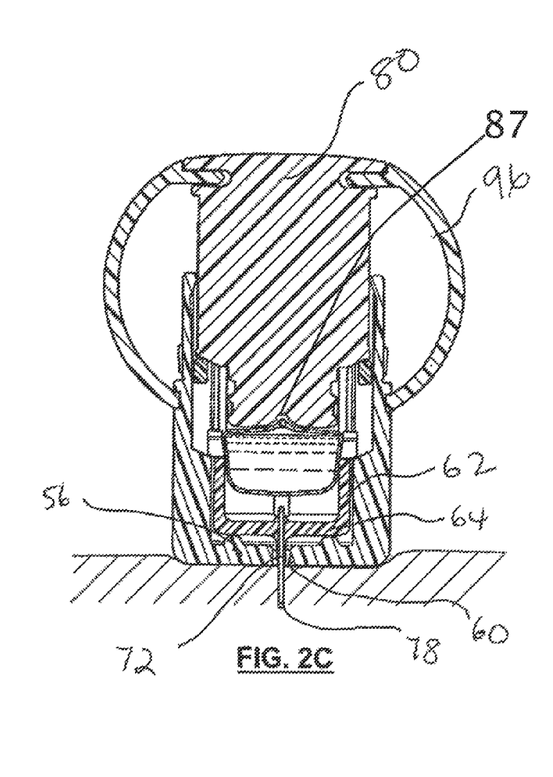
Figure 2D:
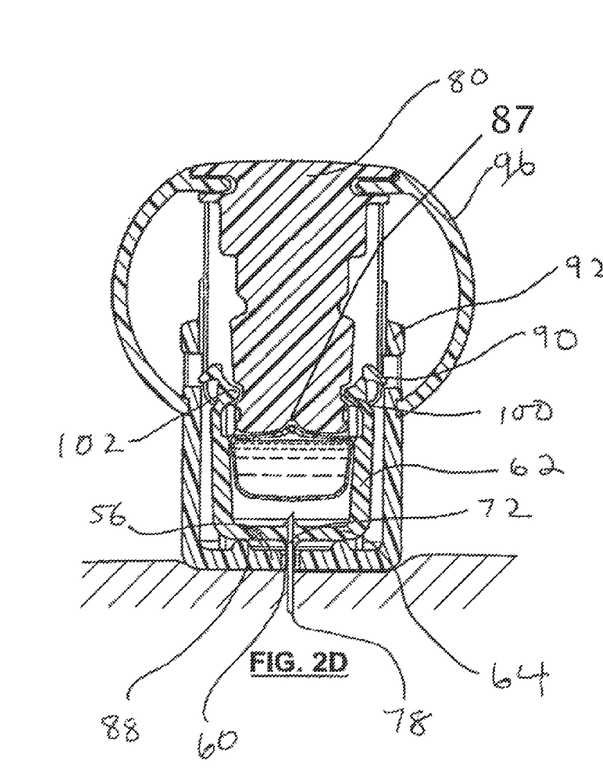
Figure 2E:
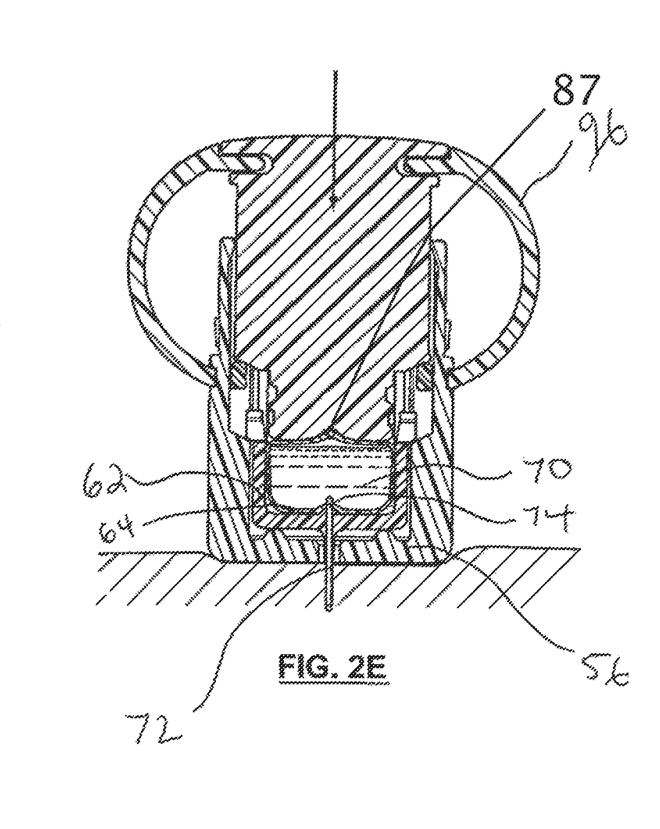
Figure 2F:
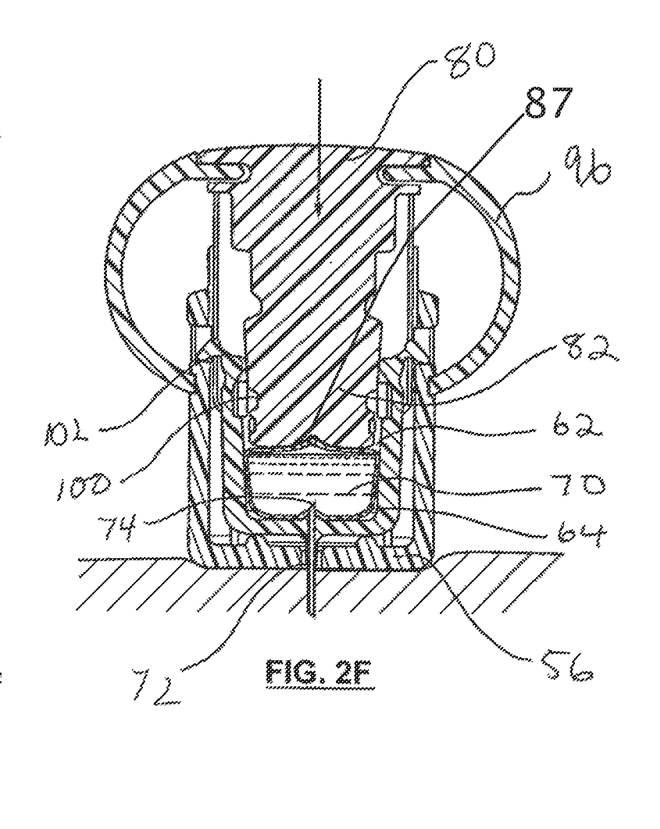
Figure 2G:
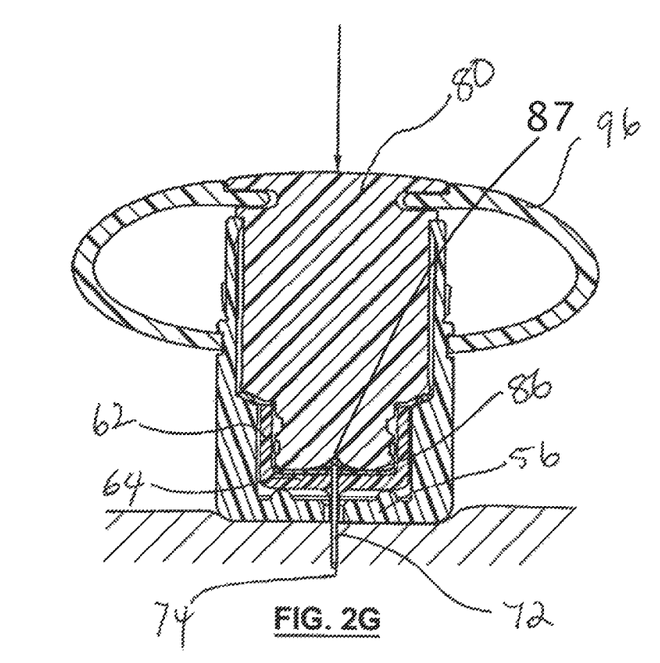

The operation of the device is illustrated sequentially in FIGS. 2A to 2J. FIGS. 2A and 2B illustrate the device in the initial state as described above. Referring now to FIGS. 2C and 2D for use, the base 56 of the housing 52 is placed against the skin. When pressure is exerted on the actuator 80, the latch 90 is released from the retainer 92. The actuator 80 is connected to the reservoir chamber 62 via a notch 100 and tab 102 connector and the reservoir chamber will be forced down until the base 64 of the reservoir chamber 62 hits the interior surface 88 of the housing base 56 and the chamber is stopped from any further downward movement. By adjusting the relative sizes and positions of the components, the length of the travel of the needle through the aperture into the skin can be tightly controlled. The distance that the needle extends is about 0.5 to 10 mm, preferably 0.5 to 5 mm, more preferably from about 3 mm to about 5 mm, even more preferably from about 1.5 to 3 mm. The outer layer of skin, the epidermis typically has a thickness of about 0.5 to 2 mm. and the inner layer, the dermis, has a thickness of about 1.5 to 3 mm. The dermis comprises two layers, the papillary layer and the reticular layer. The reticular layer contains many blood vessels and lymph vessels, making it a desirable area for delivery of active agents. Below the dermis is the subcutaneous layer and then muscle. In a preferred embodiment, the distance that the tip of the needle can extend beyond the lower outer surface of the housing is selected to be optimum for insertion in the dermis or subcutaneous layer. As the reservoir chamber 62, carrying the needle 72 descends, the lower tip of the needle 78 exits the aperture 60. The downward travel of the reservoir chamber 62 is limited when the base 64 of the chamber contacts the base 56 of the housing. In this way the travel of the needle through the aperture 60 is also limited so as to limit the depth of penetration of the needle into the skin. At this point, it is noted that the depth of the frustoconical depression 87 corresponds to the length of the upper end 74 of needle 72, such that when the base 64 of the chamber is in the downward position abutting the base 56 of the housing, and substantially all of the fluid drug is expelled from the flexible filled reservoir body 70, the upper end 74 of needle 72 fits within the frusto conical depression 87, as depicted in FIG. 2G for example. The components of the device have been configured so that the distance that the bottom of the chamber travels is translated into a predetermined travel for the needle through the aperture in the bottom of the housing to provide a certain skin penetration.

Referring now to FIGS. 2E and 2F, as continued pressure is applied to the actuator 80, the tab 102 is released from the notch 100 and the plunger 82 descends within the reservoir chamber forcing the filled reservoir 70 downwards until it contacts the base 64 of the reservoir chamber 62. As the actuator 80 exerts pressure on the reservoir 70, the reservoir 70 contacts the upper end 74 of the needle 72 and is punctured. The cannula of the needle 72 is now in fluid communication with the contents of the reservoir.

Figure 2H:
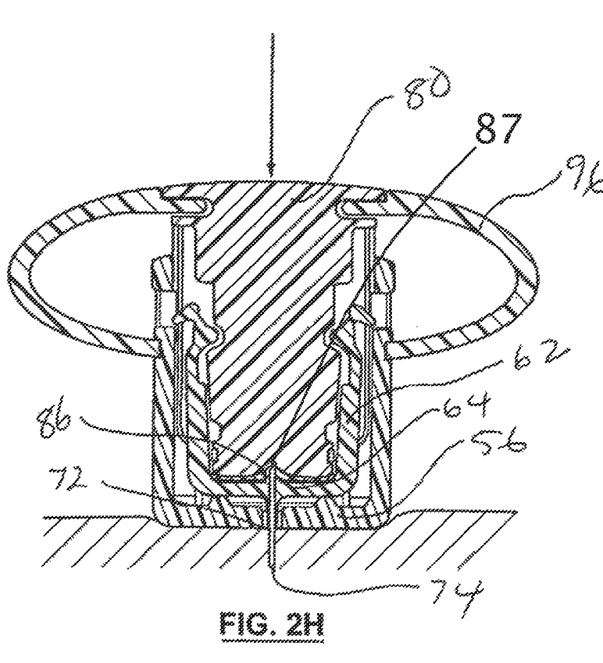

Referring now to FIGS. 2G and 2H, continued pressure on the actuator 80 compresses the reservoir 70 and forces all the contents to flow through the needle 72 and into the patient. The downward travel of the actuator 80 is stopped when the plunger stopper 86 contacts the base 64 of the reservoir chamber 62.

Figure 2I:
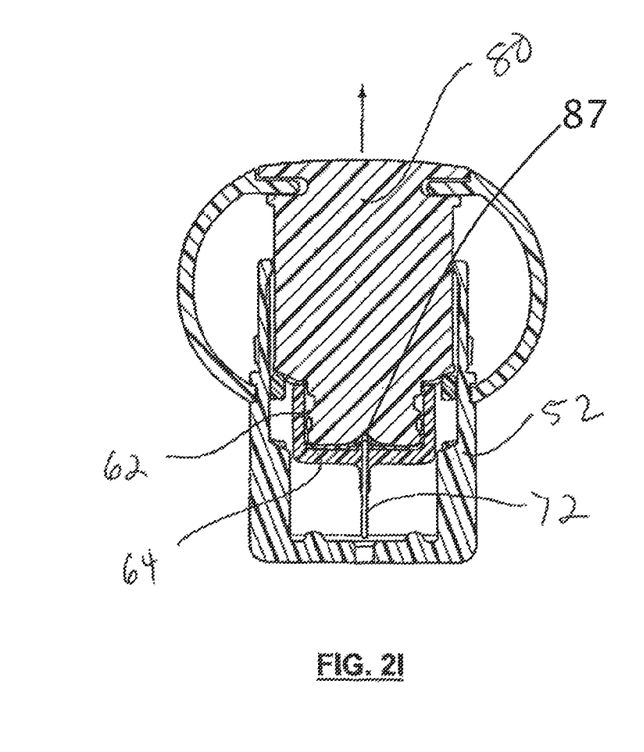
Figure 2J:
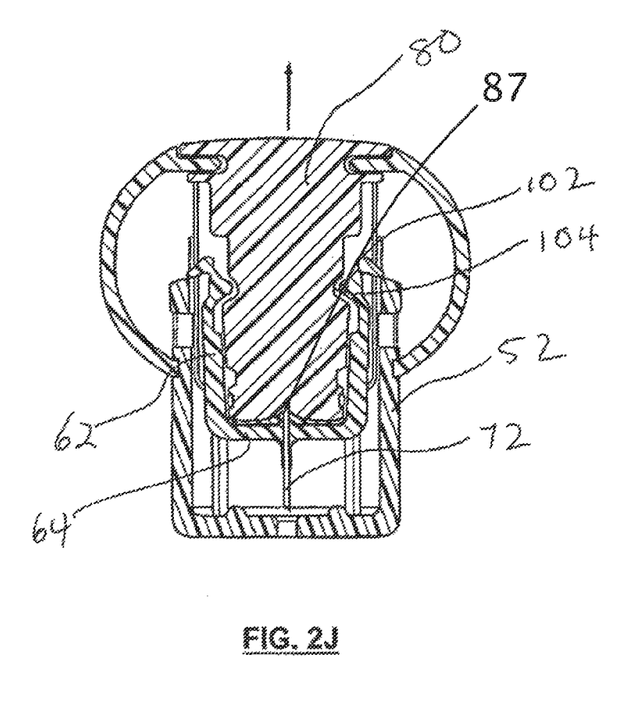

After use, the needle is preferably retracted back into the housing 52 as illustrated in FIGS. 2I and 2J. The position of the reservoir chamber 62 carrying the needle 72 is preferably biased to the pre-activation position by biasing means such as a spring, a vacuum bulb or a moldable bulb. Once pressure is released on the actuator 80, the base 64 of the reservoir chamber moves up in the housing thus automatically retracting the used needle into the housing. This provides for safe disposal of the device. In a preferred embodiment, the needle is preferably locked in the retracted position. FIG. 2J shows a retracted reservoir chamber that is locked in position when tab 102 slides into indent 104.

Figure 3A:
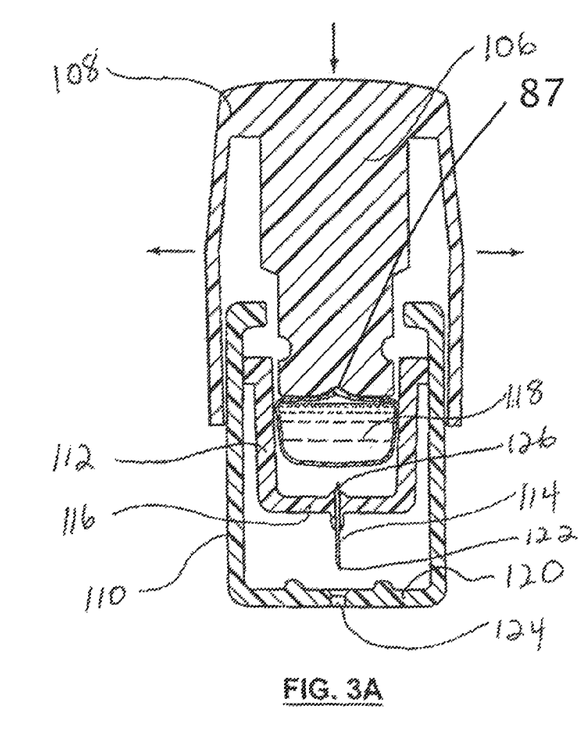
FIGS. 3A and 3B illustrate another embodiment of a delivery device.
Figure 3B:
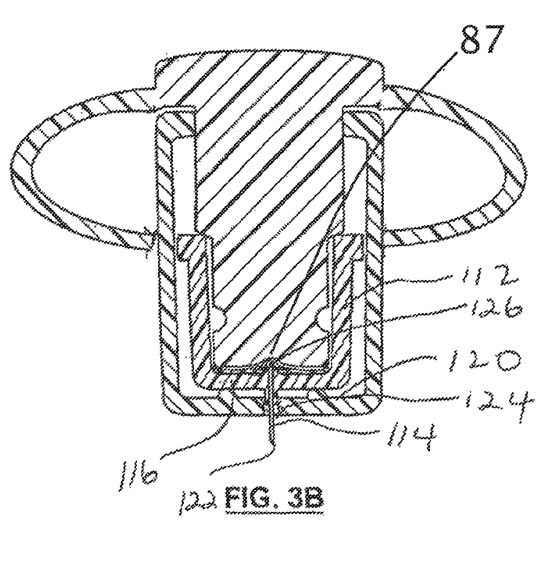

In the embodiment illustrated in FIGS. 3A and 3B, an actuator 106 is continuous with an upper casing 108 that fits over a housing 110. The housing 110 receives a reservoir chamber 112 that has a needle 114 transversely mounted through its base 116. A drug reservoir 118 is contained within the chamber 112. As shown in FIG. 3B, pressure on the actuator 106 causes the reservoir chamber 112 to descend until it abuts the base 120 of the housing 110. As the chamber 112 descends, it drives the tip 122 of the needle 114 through an aperture 124 in the housing 110. Further pressure causes the rear 126 of the needle to puncture the reservoir 118. Upon continued pressure, the contents of the reservoir are expelled through the needle.

In another embodiment, a flexible dome fits over the plunger rod and activation flange. It is also clearly apparent the manual activation flange can be exposed. The device also optionally includes a spring that is located around or below the reservoir chamber base such that when pressure on the activation flange is released the compressive energy of the spring causes the needle to be retracted back into the housing.

Figure 4A:
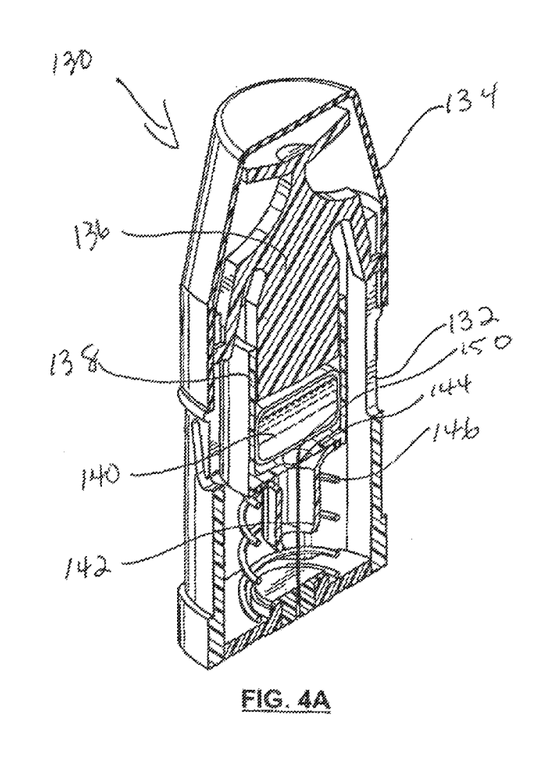
FIGS. 4A to 4C illustrate yet another embodiment of a delivery device.
Figure 4B:
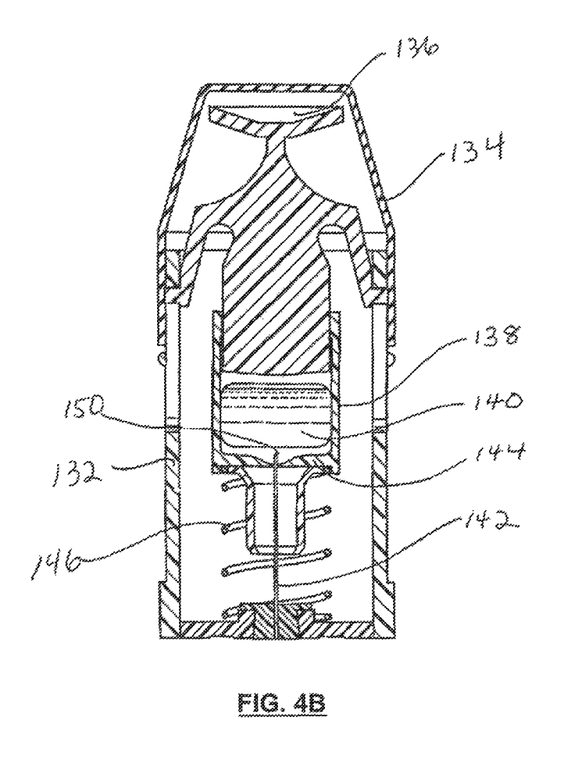
Figure 4C:
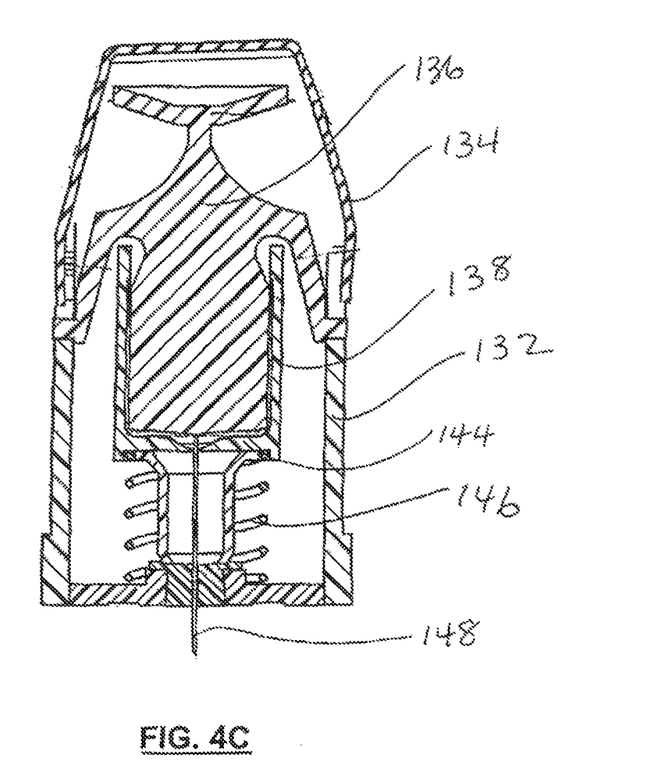

FIGS. 4A to 4C illustrate another embodiment of the device. The device 130 includes a housing 132 and an upper casing 134. An actuator 136 is operably linked to a reservoir chamber 138 disposed within the housing 132. For use, a drug filled reservoir 140 is placed in the reservoir chamber 138. A needle 142 is mounted so as to transverse the base 144 of the chamber 138. The device also includes a spring 146 that biases the reservoir chamber 138 upwards in the housing 132. Upon pressure on the actuator 136, the spring compresses and the reservoir chamber travels downward carrying the needle and the needle tip 148 exits the housing 132. Upon further pressure, the actuator 136 compresses the drug filled reservoir 140 until the back 150 of the needle punctures the reservoir and the contents flow through the needle as shown in FIG. 4C.

In another aspect of the invention, a method for delivering an effective amount of a liquid active agent to an animal, preferably a human, is provided. The method comprises providing a drug delivery device according to the present invention, said device containing a reservoir filled with the desired drug; applying the bottom surface of the drug delivery device of the invention to the skin of an animal, applying pressure on the actuator to cause the needle to enter the skin, applying continued pressure to puncture the reservoir and deliver the contents of the reservoir through the cannula of the needle.

The device of the present invention can be used to deliver a variety of active agents. The term "drug" is used loosely herein to refer to prophylactic as well as therapeutic agents. For example, vaccines may be delivered using the device. In addition, the term refers broadly to active agents, such as nucleic acids, small molecules, therapeutic proteins, hormones, analgesics, etc. in additional to traditional pharmacologic agents. Typical drugs include peptides, proteins or hormones such as insulin, calcitonin, calcitonin gene regulating protein, atrial natriuretic protein, colony stimulating factor, betaseton, erythropoietin (EPO), interferons such as $\alpha$, $\beta$, or $\gamma$ interferon, somatropin, somatotropin, somatostatin, insulin-like growth factor (somatomedins), luteinizing hormone releasing hormone (LHRH), tissue plasminogen activator (TPA), growth hormone release hormone (GHRH), oxytocin, estradiol, growth hormones, leuprolide acetate, factor VIII, interleukins such as interleukin-2, and analogues thereof; analgesics such as fentanyl, sufentanil, butorphanol, buprenorphine, levorphanol, morphine, hydromorphone, hydrocodone, oxymorephone, methadone, lidocaine, bupivacaine, diclofenac, naproxen, pavefin, and analogues thereof; anti-migraine agents such as sumatriptan, ergot alkaloids, and analogues thereof, anti-coagulant agents such as hepafin, hirudin, and analogues thereof; anti-emetic agents such as scopolamine, ondansetron, domperidone, metoclopramide, and analogues thereof; cardiovascular agents, anti-hypertensive agents and vasodilator such as diltiazem, clonidine, nifedipine, verapamil, isosorbide-5-mononitrate, organic nitrates, agents used in treatment of heart disorders, and analogues thereof; sedatives such as benzodiazepines, phenothiozines, and analogues thereof; narcotic antagonists such as naltrexone, naloxone, and analogues thereof; chelating agents such as deferoxamine, and analogues thereof; anti-diuretic agents such as desmopressin, vasopressin, and analogues thereof; antineoplastics such as 5-fluorouracil, bleomycin, and analogues thereof; prostaglandins and analogues thereof; and chemotherapy agents such as vincristine, and analogues thereof. Stabilized preparations of drugs that can be stored at room temperature are particularly preferred for use in the device and method.

The term "fluid" refers to any fluid containing an active agent or communication of agents that can pass through the cannula of the microneedle. This includes a liquid, a solution, a gel, a dispersion or a fine suspension.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A device for administering to an animal a fluid drug comprising:
    a housing having a housing open upper end and a housing bottom base defining an inner chamber;
    the housing bottom base having an aperture;
    the inner chamber adapted to slideably receive therein a reservoir chamber in an initial reservoir chamber position at a first predetermined distance from an interior surface of the housing bottom base, the reservoir chamber being confined to travel along a reservoir chamber travel path relative to the housing;
    wherein the reservoir chamber is held at the first predetermined distance by at least one releasable latch which interacts with a latch retainer on the housing open upper end, and wherein the latch includes a notch;
    the reservoir chamber defined by a reservoir chamber bottom base and surrounding wall extending from the reservoir bottom base so as provide a reservoir open top;
    the reservoir bottom base including a hollow needle having a lower end and an upper non-skin contacting end wherein the needle is mounted in and traverses the reservoir bottom base such that the upper non-skin contacting end is disposed within the interior of the reservoir chamber and just below a flexible filled reservoir body and the lower skin-contacting end can extend beyond the aperture to a second position at a predetermined distance defined by the reservoir chamber travel path of the reservoir chamber bottom base to the housing bottom base position along the reservoir chamber travel path relative the housing;
    the flexible filled reservoir body containing therein the fluid drug being located in the reservoir chamber near the reservoir open top and separated from the upper end of the hollow needle in the first predetermined reservoir chamber position; and
    an actuator having a plunger operably coupled thereto and terminating in a stopper;
    the latch being releasable from the latch retainer when pressure is applied to the actuator;
    the plunger adapted to be in slidable communication within the reservoir chamber via the reservoir open top such that, in use, the stopper can communicate with the reservoir body when in a second predetermined reservoir chamber position wherein a force being applied to the actuator causes the lower end of the hollow needle to enter the skin to the second position and further force causes the upper end of the hollow needle to pierce the reservoir body and puts the upper end of the needle into fluid communication with the contents of the reservoir body such that continuous force being applied to the actuator causes the fluid drug to be expelled through the hollow needle;
    the plunger including an indent for receiving therein a tab located on the reservoir chamber for maintaining the plunger depressed in the reservoir chamber after the fluid drug is expelled, and engagement of the tab in the indent causing the notch to engage with the latch when the reservoir chamber is returned to the initial position by biasing means whereby the needle is automatically retracted back into the housing in a locked position.

2. The device as defined in claim 1, wherein abutment of the housing bottom base with the reservoir chamber bottom base in the second predetermined reservoir chamber position acts to provide a predetermined length of travel of the hollow needle through the aperture.

3. The device as defined in claim 1, wherein the length of travel of the hollow needle in the second predetermined reservoir chamber position is from about 0.5 mm to about 10 mm extending through the aperture.

4. The device as defined in claim 1, wherein the length of travel of the hollow needle in the second predetermined reservoir chamber position is from about 1.5 mm to about 8 mm extending through the aperture.

5. The device as defined in claim 1, wherein the length of travel of the hollow needle in the second predetermined reservoir chamber position is from about 3 mm to about 8 mm extending through the aperture.

6. The device as defined in claim 1, wherein the biasing means is located within the inner chamber between the housing bottom base and the reservoir bottom base so as to bias the reservoir chamber in the first predetermined reservoir chamber position.

7. The device as defined in claim 6, wherein the biasing means is a spring.

8. The device as defined in claim 6 wherein the biasing means comprises an air bladder.

9. The device as defined in claim 1, further comprising a septum covering the aperture which is piercable by the hollow needle extending through the aperture in the second predetermined reservoir chamber position.

10. A device for administering to an animal a fluid drug comprising:
    a housing having a housing open upper end and a housing bottom base defining an interior chamber;
    the housing bottom base having an aperture therein;
    the interior chamber adapted to slideably receive therein a reservoir chamber in an initial reservoir chamber position at a first predetermined distance from the interior surface of the base of the housing, the reservoir chamber being confined to travel along a reservoir chamber travel path relative the housing; the reservoir chamber defined by a reservoir chamber bottom base and surrounding reservoir chamber wall extending from the reservoir bottom base so as provide a reservoir open top;
    the reservoir bottom base including a single hollow needle having a lower end and an upper non-skin contacting end wherein the needle is mounted in and transverses the reservoir bottom base such that the upper non-skin contacting end is disposed within the interior of the reservoir chamber and just below the reservoir and the lower skin-contacting end can extend beyond the aperture to a second position at a predetermined distance defined by the reservoir chamber travel path of the reservoir chamber bottom base to the housing base relative the housing;
    a flexible filled reservoir body containing therein the fluid drug being located in the reservoir chamber near the reservoir open top and separated from the upper end of the hollow needle in the first predetermined reservoir chamber position; and an actuator having a plunger operably coupled thereto and terminating in a stopper, the stopper having formed therein a frustoconical depression; the frustoconical depression having a depth corresponding to the length of the upper non-skin contacting end of the needle disposed within the interior of the reservoir chamber;

the plunger adapted to be in slidable communication within the reservoir chamber via the reservoir open top such that, in use, the stopper can communicate with the flexible filled reservoir body with a portion of the flexible filled reservoir body being received in the depression when in a second predetermined reservoir chamber position, wherein a force being applied to the actuator causes the lower end of the hollow needle to enter the skin to the second position and further force causes the upper end of the hollow needle to pierce the reservoir body and puts the upper end of the needle into fluid communication with the contents of the flexible filled reservoir body such that continuous force being applied to the actuator causes the stopper to compress the flexible filled reservoir body and the fluid drug through the hollow needle and wherein the upper non-skin contacting end of the needle is located within a portion of the flexible filled reservoir body received in the depression once substantially all of the fluid drug is expelled;

the reservoir chamber is held at said first predetermined distance by at least one releasable latch;

said at least one releasable latch engagable with a latch retainer located on said housing upper end;

said at least one releasable latch including a notch;

said at least one releasable latch being released from said latch retainer when sufficient pressure is applied to said actuator;

said plunger including an indent for receiving therein a tab located on the reservoir chamber for maintaining said plunger depressed in said reservoir chamber after the fluid drug is expelled and engaging the tab in the indent causes the notch to engage with said at least one releasable latch when the reservoir chamber is returned to the said initial position by biasing means thereby retracting and locking said lower skin-contacting end of said needle within said housing.

11. The device as defined in claim 10, wherein abutment of the housing bottom base with the reservoir chamber bottom base in the second predetermined reservoir chamber position acts to provide a predetermined length of travel of the hollow needle through the aperture.

12. The device as defined in claim 10, wherein the biasing means is located within the inner chamber between the housing bottom base and the reservoir bottom base so as to bias the reservoir chamber in the initial reservoir chamber position.

13. The device as defined in claim 12, wherein the biasing means is a spring.

* * * * *